United States Patent
Ranjekar et al.

(10) Patent No.: US 6,180,345 B1
(45) Date of Patent: Jan. 30, 2001

(54) PROCESS FOR SIMULTANEOUS PREPARATION OF SEX SPECIFIC AND GENDER-NEUTRAL SEMISYNTHETIC AMPLICONS USEFUL FOR SEX DETERMINATION

(75) Inventors: Prabhakar K. Ranjekar; Anjali S. Parasnis; Vidya S. Gupta, all of Pune (IN)

(73) Assignee: Counsel of Scientific & Industrial Research, New Delhi (IN)

( * ) Notice: Under 35 U.S.C. 154(b), the term of this patent shall be extended for 0 days.

(21) Appl. No.: 09/259,473

(22) Filed: Feb. 26, 1999

Related U.S. Application Data

(63) Continuation-in-part of application No. 09/052,505, filed on Mar. 31, 1998, now Pat. No. 6,037,128.

(30) Foreign Application Priority Data

Aug. 13, 1998 (IN) ............................................. 2377/DEL/98

(51) Int. Cl.$^7$ .............................. C12Q 1/68; C12P 19/34; C07H 21/02; C07H 21/04
(52) U.S. Cl. ............................ 435/6; 435/91.2; 435/91.5; 536/23.1; 536/23.6; 536/24.3; 536/24.33
(58) Field of Search ............................ 435/6, 91.2, 91.5; 536/23.1, 23.6, 24.3, 24.33

(56) References Cited

U.S. PATENT DOCUMENTS 5,747,257  5/1998  Jensen ....................................... 435/6

OTHER PUBLICATIONS

Jones et al., "Refined Papain", *Process Biochemistry* vol. 9, No. 6 pp 21–24 (1974).

Madrigal et al., "The Dependence of Crude Papain Yields on Different Collection ('Tapping') Procedures for Papaya Latex", *J. Sci. Food Agric.* 31, 279–285 (1980).

Polley et al., "Identification of sex in hop (Humulus Lupulus) using molecular markers", *Genome*, 40: 357–361 (1997).

Sondur et al., "A genetic linkage map of papaya based on randomly amplified polymorphic DNA markers", *Theor Appl Genet*, 93: 547–553 (1996).

Taberlet et al., "Universal primers for amplication of three non–coding regions of chloroplast DNA", *Plant Molecular Biology* 17:1105–1109 (1991).

*Primary Examiner*—Carla J. Myers
*Assistant Examiner*—Diana Johannsen
(74) *Attorney, Agent, or Firm*—Fish & Richardson P.C.

(57) ABSTRACT

An improved process for simultaneous preparation of sex specific and gender-neutral semisynthetic amplicons obtained by amplifying sequences of synthetic oligonucleotide primers identified as SEQ ID NOS:4 to 7 (5'GGATCCCTATlAGTG 3'; 5'GGATCCCITTTGCACTC 3'; 5CGAAATCGGTAGACGATACG3' and 5'GGGGATA-GAGGGACTTGAAC 3') useful for sex determination, said process comprising isolating nucleic acids from any part of a papaya plant by conventional methods, amplifying the said nucleic acids in a conventional Random Amplification of polymorphic DNA Polymerase Chain Reaction (RAPD-PCR), resolving the amplified products by conventional electrophoresis method, eluting the sex specific, double stranded amplified product from the gel piece by known methods, cloning the said product in a known vector by conventional methods, sequencing the said cloned product by known methods, synthesizing the single stranded chains of synthetic oligonucleotides by known method based on the said sequence data, amplifying the said nucleic acid in a Conventional Sequence Tagged Site Polymerase Chain Reaction by using synthetic oligonucleotides as primers to get sex specific and gender-neutral semisynthetic amplicons simultaneously.

12 Claims, No Drawings

SEQUENCE LISTING

<160> NUMBER OF SEQ ID NOS: 7

<210> SEQ ID NO 1
<211> LENGTH: 831
<212> TYPE: DNA
<213> ORGANISM: Papya cultivar pusa-giant

<400> SEQUENCE: 1

| | | | | | |
|---|---|---|---|---|---|
| gaggatccct | attagtgtaa | gggatgttca | agaacctagc | tctgatatca | cctatgacat | 60 |
| ctcggtaccg | aatagggcaa | cggtgtctga | caacataata | gatatgagtg | cataaaagaa | 120 |
| ctatacaaca | gaagaaaagt | catttcttat | aaaaatttga | tgtttaaata | catttgagat | 180 |
| caagaacttg | gtagttaaaa | tatatacaag | cattattata | tcaacttcta | tattacaaaa | 240 |
| taattgttta | tcagagtaca | ataattcaca | tgcacttaaa | ttacgctaca | agttcacgaa | 300 |
| caaatccaaa | caaactttaa | tggtgcagtt | tgagcagcag | caatcttcac | tttcgtatct | 360 |
| ctagggaaa | tagagttggg | gtgactttca | taagactcag | taaactctgt | acggaaaata | 420 |
| gtatttaaaa | tacggtaata | aaggtttaaa | ggttgtttat | tttaaaaatg | tgtcatacct | 480 |
| tttcattcaa | tagagcttac | cgtcagagtc | cgttgcagat | taaattcatt | taaaatacta | 540 |
| ctaaaaagtt | catacttttg | gttaattgaa | atacatttta | aaataccaaa | atttcaaaca | 600 |
| taagcagtaa | aactgaatga | gaaacatatt | tggaaccagt | ggaattatct | aaacatagaa | 660 |
| agacgagaca | gagtagtgag | aaacatagca | aactcaacat | gcggtcaaaa | tcatagaaat | 720 |
| aaatcaatag | tcctagctag | caattaaact | atttggttca | attacagtgt | tttacagatc | 780 |
| ttcacacaaa | gccattttaa | cttatatcag | cagagtgcaa | aagggatcct | c | 831 |

<210> SEQ ID NO 2
<211> LENGTH: 21
<212> TYPE: DNA
<213> ORGANISM: Papya cultivar pusa-giant

<400> SEQUENCE: 2
ggatccctat tagtgtaagg g          21

<210> SEQ ID NO 3
<211> LENGTH: 22
<212> TYPE: DNA
<213> ORGANISM: Papya cultivar pusa-giant

<400> SEQUENCE: 3
ggatcccttt tgcactctgc tg          22

<210> SEQ ID NO 4
<211> LENGTH: 15
<212> TYPE: DNA
<213> ORGANISM: Papya cultivar pusa-giant

<400> SEQUENCE: 4
ggatccctat tagtg          15

<210> SEQ ID NO 5
<211> LENGTH: 17
<212> TYPE: DNA
<213> ORGANISM: Papya cultivar pusa-giant

<400> SEQUENCE: 5
ggatcccttt tgcactc          17

-continued

```
<210> SEQ ID NO 6
<211> LENGTH: 20
<212> TYPE: DNA
<213> ORGANISM: Papya cultivar pusa-giant

<400> SEQUENCE: 6
cgaaatcggt agacgatacg                                                    20

<210> SEQ ID NO 7
<211> LENGTH: 20
<212> TYPE: DNA
<213> ORGANISM: Papya cultivar pusa-giant

<400> SEQUENCE: 7
ggggatagag ggacttgaac                                                    20
```

PROCESS FOR SIMULTANEOUS PREPARATION OF SEX SPECIFIC AND GENDER-NEUTRAL SEMISYNTHETIC AMPLICONS USEFUL FOR SEX DETERMINATION

This application is a continuation-in-part of U.S. application Ser. No. 09/052,505, filed Mar. 31, 1998, now U.S. Pat. No. 6,037,128, the disclosure of which is considered part of and is incorporated into the present application by reference.

FIELD OF THE INVENTION

This invention relates to an improved process for simultaneous preparation of sex specific and gender-neutral semisynthetic amplicons useful for sex determination.

This invention particularly relates to an improved process for simultaneous preparation of sex specific and gender-neutral semisynthetic amplicons useful for sex determination. The invention particularly relates to a process for simultaneous preparation of sex specific and gender-neutral semisynthetic amplicons useful for sex determination of papaya plants. The process involves amplification of nucleic acid in a Polymerase Chain Reaction (PCR) using synthetic oligonucleotide primers.

BACKGROUND

Carica papaya commonly known as papaya, is a native of tropical America. It belongs to the genus Carica, a member of family caricaceae. The plant adopts itself to diverse soil and climatic conditions, and hence is grown extensively in tropical and subtropical areas for its profitable and continuous yield of fruits. The fruits are mostly consumed ripe and are a rich source of vitamins A, B, C, and D (Kumar et al. J. Born Natural His. Society, Vol XV, No. 2. Dec. 43, 252–256). Thin, milky latex is extracted out of young green fruits. This latex contains a high percentage of papain, which is one of the most valuable of plant proteolytic enzymes. Papain is of interest to many industries among which food industry is one of the biggest consumers. Papain is used for chillproofing beer, tenderizing meat and freeing food proteins. It is used in peptone preparation from meat and milk in bacteriological laboratories, in textile industry for degumming of silk, in dairy industry for cheese preparation, in tanning industry for skin dehairing and bating of hides, in pharmaceutical industry, perfume industry and in effluent treatment. Papain is also used to produce animal feed products and recover animal wastes by digestion of proteins. (Jones et al, Process Biochemistry 9, 1976, 21–24).

Papaya plants are propagated through seeds. The seeds are sown in seedbeds and 1–2 months old seedlings are transplanted to the field. 2–3 seedlings are planted in one pit, as the sex of the seedlings is unknown. Plants attain reproductive maturity after 5–8 months. Most of the male plants are then uprooted from the field. This unnecessary cultivation and uprooting leads to wastage of time, money and labor.

The dioecious cultivars are preferred for the extraction of papain as the female yields of crude papain exceed that of hermaphrodite and also the proteolytic activity of the crude papain from female fruits is greater than hermaphrodites (Madrigal et al., J. Sci. Food Agri. 1980, 31: 279–285).

Breeding programs are initiated with objectives to evolve disease resistant and true breeding papaya varieties with good quality fruits and high papain content. The dioecious nature poses problems and inconvenience to papaya breeders and growers since it takes 5–8 months to known the sex of the seeding. Unfortunately, sex cannot be deduced from external morphology or cytology with embryonic or juvenile forms. If the sex of plants is known at the juvenile stage, it would facilitate screening of the seedlings for female plants saving time and economic resources and thereby helping in the breeding program.

In our unpublished copending Indian Patent Application No. 268/Del/97, a process for preparation of duplex polynucleotide useful for sex determination of papaya plant has been reported. In our other unpublished copending Indian Patent Application No. 2447/Del/97 which corresponds to U.S. Ser. No. 09/052,505 filed on Mar. 31, 1998, now U.S. Pat. No. 6,037,128, a process for preparation of semisynthetic amplicon useful for sex determination of the papaya plant has been described. However, the present application more accurate and an improved process for preparation of sex specific and gender-neutral amplicons useful for sex determination. Apart from patent applications, there is no prior art available identification of sex of dioecious papaya plant describes still simultaneous semisynthetic our own-filed patent applications, there is no prior art available for the identification of sex of dioecious papaya plant.

SUMMARY

The objective of the present invention is to provide an improved process for simultaneous preparation of sex specific and gender-neutral semisynthetic amplicons useful for sex determination.

Another objective of the present invention is to provide a process for simultaneous preparation of sex specific and gender-neutral semisynthetic amplicons useful for sex determination of papaya plants.

Yet another objective of the present invention is to provide a process for simultaneous preparation of sex specific and gender-neutral semisynthetic amplicons useful for sex determination of papaya plants at juvenile stage.

DETAILED DESCRIPTION OF INVENTION

Accordingly, the present invention provides an improved process for simultaneous preparation of sex specific and gender-neutral semisynthetic amplicons useful for sex determination, which comprises, isolating nucleic acids from any part of a papaya plant by conventional methods, amplifying the said nucleic acids in a conventional Random Amplification of polymorphic DNA polymerase Chain Reaction (RAPD-PCR), resolving the amplified products by conventional electrophoresis method, eluting the sex specific, double stranded amplified product from the gel piece by known methods, cloning the said product in a known vector by conventional methods, sequencing the said cloned product by known methods, synthesizing the single stranded chains of synthetic oligonucleotides by known method based on the said sequence data, amplifying the said nucleic acid in a conventional Sequence Tagged Site Polymerase Chain Reaction by using synthetic oligonucleotides as primers to get sex specific and gender-neutral semisynthetic amplicons simultaneously.

In an embodiment of the present invention, isolation of nucleic acid can be carried out by conventional method such as Roger & Bendich method from any part of a papaya plant such as leaf, root, petiole. In an embodiment of the present invention, the polymerase chain reaction is carried out by using a thermostable DNA polymerase enzyme.

In another embodiment of the present invention, the Random Amplification of polymorphic DNA Polymerase Chain Reaction (RAPD-PCR) may be effected by using one or more stranded oligonucleotide primers, such as 5–12 mer primers, preferably known decamers.

In another embodiment of the present invention separation of the products of Polymerase Chain Reaction may be effected by conventional electrophoresis method using agarose gel, polyacrylamide gel and mixtures thereof.

In an embodiment of the present invention, elution of the sex specific amplification product from the gel piece may be effected by conventional elution methods, such as electroelution, freeze-thaw method.

In an embodiment of the present invention, cloning of the sex specific amplified, eluted product may be effected by using a plasmid vector, such as PCR product cloning vector.

In a feature of the present invention sequencing of the cloned product is effected by known methods, such as Sanger's chain termination method.

In another embodiment of the present invention the cloned semisynthetic amplicon has the following sequence.

Spring Harbor Laboratory, NY (1985) and by Roger & Bendich (Roger et al, 1988, PMB manual A6 1 Ed).

In a process of this invention oligonucleotide primers can be prepared by any suitable method for example, direct chemical synthesis by using phosphoramidite chemistry (Gait M. J., Oligonucleotide synthesis a practical approach, IRL press Ltd).

Since the PCR reaction is supersensitive, minute contamination of the undesirable DNA or deviation in the experimental conditions may affect the amplification signal, the possibility exists that male samples will not show male signals. In order to avoid this and to verify accuracy of sex diagnosis, PCR primers giving a gender-neutral signal are needed.

The gender-neutral oligonucleotide primers can be designed based on any suitable and known DNA sequence. For example the PCR primers designed from the chloroplast and mitochondrial DNA sequences as described by Taberlet et. al. (PMB17: 1105–1109,1991).

Primers for the PCR reaction described above have to be selected carefully to meet two criteria. The lengths of PCR

```
GAGGATCCCT ATTAGTGTAA GGGATGTTCA AGAACCTAGC TCTGATATCA  50

CCTATGACAT CTCGGTACCG AATAGGGCAA CGGTGTCTGA CAACATAATA 100

GATATGAGTG CATAAAAGAA CTATACAACA GAAGAAAAGT CATTTCTTAT 150

AAAAATTTGA TGTTTAAATA CATTTGAGAT CAAGAACTTG GTAGTTAAAA 200

TATATAACAAGCATTATTATA TCAACTTCTA TATTACAAAA TAATTGTTTA 250

TCAGAGTACA ATAATTCACA TGCACTTAAA TTACGCTACA AGTTCACGAA 300

CAAATCCAAA CAAACTTTAA TGGTGCAGTT TGAGCAGCAG CAATCTTCAC 350

TTTCGTATCT CTAGGGGAAA TAGAGTTGGG GTGACTTTCA TAAGACTCAG 400

TAAACTCTGT ACGGAAAATA GTATTTAAAA TACGGTAATA AAGGTTTAAA 450

GGTTGTTTAT TTTAAAAATG TGTCATACCT TTTCATTCAA TAGAGCTTAC 500

CGTCAGAGTC CGTTGCAGAT TAAATTCATT TAAAATACTA CTAAAAAGTT 550

CATACTTTTG GTTAATTGAA ATACATTTTA AAATACCAAA ATTTCAAACA 600

TAAGCAGTAA AACTGAATGA GAAACATATT TGGAACCAGT GGAATTATCT 650

AAACATAGAA AGACGAGACA GAGTAGTGAG AAACATAGCA AACTCAACAT 700

GCGGTCAAAA TCATAGAAAT AAATCAATAG TCCTAGCTAG CAATTAAACT 750

ATTTGGTTCA ATTACAGTGT TTTACAGATC TTCACACAAA GCCATTTTAA 800

CTTATATCAG CAGAGTGCAA AAGGGATCCT C(SEQ ID NO:1)       831
```

In an another embodiment of the present invention, simultaneous preparation of sex specific and gender-neutral semisynthetic amplicons may be effected by conventional Sequence Tagged Site Polymerase Chain Reaction by using synthetic oligonucleotide primers, such as primers spanning the sequence of the said sex specific semisynthetic amplicon and synthetic oligonucleotide primers based on the known sequence data such as chloroplast DNA sequence, mitochondrial DNA sequence and combinations thereof.

In a process of the present invention, DNA can be isolated from a variety of tissues including leaf, anther, ovary, seed, stem and root. The choice of tissue depends on many factors, including the quantity of the starting material required and difficulty in isolating DNA from a particular tissue. A variety of techniques for extracting nucleic acids from biological samples are known, for example those described by Sambrook et al, Molecular Cloning—A laboratory manual, Cold products need to be sufficiently different to allow clear differentiation between the male-specific sequence and the gender-neutral one. Secondly, the lengths of the anticipated PCR amplification products preferably should not be longer than a length compatible with the activity of DNA polymerase. The difference of the length of PCR products should preferably around 50–100 bases.

After the PCR reaction is allowed to proceed, the PCR products are analyzed by gel electrophoresis and stained with a fluorescence dye, the DNA samples which reveal two semisynthetic amplicons, one sex-specific whereas the second being gender-neural are male while the DNA samples which exhibit a single gender-neutral semisynthetic amplicon are female.

In a process of this invention, the amplified products of a polymerase chain reaction may be resolved by known methods for example, on agarose gel, on polyacrylamide gel, on a mixture of polyacrylamide and agarose, as described in Maniatis et al, *Molecular Cloning: A Laboratory Manual*, Cold Spring Harbor, NY: Cold Spring Harbor Laboratory, 1982.

In the process of this invention detection of the resolved amplified products on the gel can be carried out by various conventional methods for example autoradiography of the gel, staining of the gel by known methods, such as, ethidium bromide staining, silver staining as mentioned in Maniatis et al, *Molecular Cloning: A Laboratory Manual*, Cold Spring Harbor, NY: Cold Spring Harbor Laboratory, 1982.

In a process of the present invention, oligonucleotide primers and nucleotides used in the polymerase chain reaction may be detectably labelled, using any reporter element that is capable of generating a detectable signal. Such detectable labels include radioactive markers such as $^{32}P$, $^3H$, $^{14}C$ or $^{125}I$, and non-radioactive markers, such as alkaline phosphate, biotin bromodeoxyuridine, fluorescent or chromogenic molecules.

The term "oligonucleotide" refers to a molecule comprising of two or more deoxyribonucleotides or ribonucleotides.

The term "Polymerase Chain Reaction (PCR)" is an in vitro method of nucleic acid synthesis by which a particular segment of DNA can be specifically replicated. The process of PCR involves repeated cycles of heat denaturation of the DNA, annealing of the primers to their complementary sequences and extension of the annealed primers with thermostable DNA Polymerase.

The term "primer" refers to an oligonucleotide, whether natural or synthetic, capable of acting as a point of initiation of DNA synthesis complementary to a nucleic acid strand, in the presence of four different nucleoside triphosphates and an agent for polymerization (i.e. DNA polymerase or reverse transcirptase). The term "semisynthetic amplicon" refers to a deoxyribonucleotide polymer in double-stranded form, amplified artificially in a polymerase chain reaction. The amplicon is biologically inactive and cannot replicate on its own.

Amplifying or amplification, as used herein describes both linear and exponential increase in the number of target sequence of nucleic acid.

The term "Random Amplification of polymorphic DNA Polymerase Chain Reaction (RAPD-PCR)" as used herein describes a process wherein exponential increase in the number of target sequence of nucleic acid takes place by using random decamer primers having arbitrary sequence.

The term "Sequence Tagged Site Polymerase Chain Reaction" as used herein describes a process wherein exponential increase in the number of selected target sequence of nucleic acid takes place by a pair of specific primers having sequence specificity to the selected target sequence.

The term "gender-neutral semisynthetic amplicon" as used herein refers to the product amplified irrespective of the gender of the plant i.e. amplified in both male and female DNA samples.

The method of the present invention is described herein below with reference to examples, which are illustrative only and should not be construed to limit the scope of the present invention in any manner.

The following example relates to the simultaneous preparation of sex specific and gender-neutral semisynthetic amplicons useful for determination of sex in papaya plants.

EXAMPLE 1

Matured male and female plants of dioecious papaya cultivar PUSA-GIANT were identified in the field. Young leaf tissue from both male and female individuals of this cultivar was harvested and frozen in liquid nitrogen. Ten grams of the frozen tissue of each sample was mechanically ground to a fine powder using pestle and mortar in liquid nitrogen.

The DNA isolations were carried out by Roger and Bendich method (Roger, 1988, PMB manual, A6 1 Ed), where 15 ml of extraction buffer containing 2% CTAB (Cetyltriethyl ammonium bromide), 100 mM Tris-HCl (pH 8.0), 20 mM EDTA (pH 8.0), 1.4 M NaCI, and 1% polyvinyl pyrrolidone was added per 10gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supenatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [IM NaCI, 10 mM Tris-HCI (pH 8.0), 1 mM EDTA (pH 8.0)] and was precipitated with twice the volume of absolute ethanol. The DNA precipitate was washed with 70% ethanol, centrifuged and the pellet was dissolved in TE buffer [10 mM Tris-HCI (pH 8.0), 1 mM EDTA (pH 8.0)]. For removal of RNA, the DNA was incubated at 37° C. for 1 hour with the enzyme RNaseA.

The isolated DNA was quantified spectrophotometrically and subjected to Random Amplification of polymorphic DNA Polymerase Chain Reaction (PAPD-PCR) with a synthetic, arbitrary, 10 bp primer. The final volume of the reaction mixture was 25 $\mu l$, which contained 20ng of template DNA, 1.5 mM MgCI, 50 mM KCI, 10 mM TAPS [3-W (hydroxymethyl) methyl amino propane sulphonic acid], 0.01% gelatine, 100 $\mu m$ of each dATP, dCTP, dGTP and dTTP, 25 $\mu m$ spermidine, 0.6 Units of thermostable DNA polymerase and 15 pmoles of decamer primer having the sequence 5'GAGGATCCCT 3' (nucleotides 1–10 of SEQ ID NO:1). The reaction mixture was overlaid with 30 $\mu l$ of mineral oil and spun for 30 sec. at 1000rpm.

Amplification reaction was performed in a thermocycler, where the reaction mixture was incubated at 94° C. for 5 minutes, followed by 45 cycles of 94° C. for 1 minute, 36° C. for 1 minute and 72° C. for 2 minutes each. The amplification reaction was concluded by a final extension of 72° C. for 5 minutes. The amplification products were analyzed on 1.8% neutral agarose horizontal slab gel in TAE buffer (40.0mM Tris-acetate and 2 mM EDTA) at a constant current. After electrophoresis, gel was stained with ethidium bromide (1 $\mu g/ml$) and was visualised on a long wavelength (302 nm) UV transilluminator.

A sex specific amplicon having molecular weight of 0.8 Kb was identified in the male individual. A gel-slice containing DNA of the sex specific amplicon was cut out from the gel using a sharp blade and the DNA was eluted from the gel piece as described in Maniatis et al, *Molecular Cloning: A Laboratory Manual*, Cold Spring Harbor, NY: Cold Spring Harbor Laboratory, 1982.

100ng of the eluted DNA was ligated to 100ng of a PCR product cloning vector in a reaction containing, 1 $\mu g$ 10X DNA ligase buffer [500mM Tris-HCI (pH 7.4), 100mM spermidine, 1 mg/ml BSA (Bovine Serum Albumin)], 1 $\mu l$ of 1M ATP, 1 $\mu l$ of 0.1 M MgCl2 and 2.0U of the enzyme DNA ligase. Final volume of the reaction was adjusted to 10 $\mu l$ by adding sterile water. The ligation reaction was carried out at 16° C. for 16 hours and the ligated products were directly transformed into the competent cells of *E. coli*. The transformed *E. coli* cells were plated on LB (Luna-Bertani) medium [Bacto tryptone 10 gm/lit, Bacto yeast extract 5 gm/lit, Sodium chloride 10 gm/lit] containing the antibiotic ampicillin (100 $\mu g/ml$). Resulting colonies were screened for the presence of the recombinants as described in Maniatis et al, *Molecular Cloning: A Laboratory Manual*, Cold Spring Harbor, NY: Cold Spring Harbor Laboratory, 1982. The plasmid DNA was isolated by inoculating a colony positive for the insert in 1 ml LB medium containing the antibiotic ampicillin (100 µ/mI). The culture was grown at 37° C., for 16 hours with constant shaking at 175rpm. The culture was spun in 1.5 ml plastic tube for 10 minutes to pellet the cells and the supernatant was discarded. The cell pellet was suspended in a 10 µl solution of GTE buffer [50mM Glucose, 25mM Tris-HCI (pH 8.0), and 10mM EDTA (pH 8.0)], vortexed and incubated at room temperature for ten minutes. 200 µl of freshly prepared solution containing 1% SDS and 0.2N NaOH was added to the cell suspension, mixed well by tapping the tube and incubated on ice for ten minutes and further purified as described by Maniatis et al [Molecular Cloning: A Laboratory Manual, Cold Spring Harbor, NY: Cold Spring Harbor Laboratory, 1982].

The cloned sex specific semisynthetic amplicon was sequenced by Sanger's dideoxy chain termination method, as described by Sanger et al, *PNAS* 74,1977: 54–63.

To denature the template DNA, 2 µg of plasmid DNA was dried in a centrifuge tube and dissolved in 40 µl denaturation primer mixture was added to each of the labelled tubes, mixed and incubated at 37° C. for 5 minutes. After the incubation, 40 of formamide buffer (95% Formamide, 20 mM EDTA, O. 0.05% Bromophenol Blue, 0.05% Xylene Cyanol FF) was added to stop the reaction.

The sequencing reaction was then resolved on a 6%, 0.4 mm thick, denaturing polyacrylamide gel. Electrophoresis was carried out at a constant voltage (2000 V) in 1XTBE buffer (89mM Tris-borate and 2 mM EDTA). After the electrophoresis, the gel was covered in thin plastic sheet and exposed to an X-ray film at −70° C. for 16 hours.

Sequencing of the cloned sex specific semisynthetic amplicon revealed a sequence as shown in SEQ ID NO:1.

```
SEQ ID NO:1
GAGGATCCCT ATTAGTGTAA GGGATGTTCA AGAACCTAGC TCTGATATCA   50

CCTATGACAT CTCGGTACCG AATAGGGCAA CGGTGTCTGA CAACATAATA  100

GATATGAGTG CATAAAAGAA CTATACAACA GAAGAAAAGT CATTTCTTAT  150

AAAAATTTGA TGTTTAAATA CATTTGAGAT CAAGAACTTG GTAGTTAAAA  200

TATATAACAAGCATTATTATA TCAACTTCTA TATTACAAAA TAATTGTTTA  250

TCAGAGTACA ATAATTCACA TGCACTTAAA TTACGCTACA AGTTCACGAA  300

CAAATCCAAA CAAACTTTAA TGGTGCAGTT TGAGCAGCAG CAATCTTCAC  350

TTTCGTATCT CTAGGGGAAA TAGAGTTGGG GTGACTTTCA TAAGACTCAG  400

TAAACTCTGT ACGGAAAATA GTATTTAAAA TACGGTAATA AAGGTTTAAA  450

GGTTGTTTAT TTTAAAAATG TGTCATACCT TTTCATTCAA TAGAGCTTAC  500

CGTCAGAGTC CGTTGCAGAT TAAATTCATT TAAAATACTA CTAAAAAGTT  550

CATACTTTTG GTTAATTGAA ATACATTTTA AAATACCAAA ATTTCAAACA  600

TAAGCAGTAA AACTGAATGA GAAACATATT TGGAACCAGT GGAATTATCT  650

AAACATAGAA AGACGAGACA GAGTAGTGAG AAACATAGCA AACTCAACAT  700

GCGGTCAAAA TCATAGAAAT AAATCAATAG TCCTAGCTAG CAATTAAACT  750

ATTTGGTTCA ATTACAGTGT TTTACAGATC TTCACACAAA GCCATTTTAA  800

CCTATATCAG CAGAGTGCAA AAGGGATCCT C(SEQ ID NO:1)         831
``` buffer (0.2MNaOH, 0.2mM EDTA, pH 8.0) and kept at 37° C. for 30 minutes. 4 µl of 3M Sodium acetate, pH 5.2 was added, followed by 100 µl of chilled ethanol and precipitated for 30 minutes at −70° C. The sample was spun at 10,000 rpm for 10 minutes at 4° C. Supernatant was discarded and pellet was washed with 70% ethanol, dried and dissolved in 7 µl of sterile water.

To anneal the sequencing primer to the template DNA, 1 µl of sequencing primer and 2 µl of 5X reaction buffer were added to the template DNA and incubated at 65° C. for 2 minutes.

The labelling reaction was carried out by adding, 1 µl DTT(0.1 M), 2 µl labelling nucleotide mix (7.5 µm dGTP, 7.5 µm dTTP, 7.5 µm dCTP), 5 µCi of α-³²P dATP and 0.6 units of enzyme to the annealed template-primer. The sample was incubated for 5 minutes at room temperature.

Two microliters of dideoxynucleotide mixture (ddGTP, ddCTP, ddATP and ddTTP) was taken in four labelled tubes and warmed to 37° C. for 2 minutes. 3.5 µl of the template Based on the sequence data as mentioned in SEQ ID NO:1, the primers were designed so as to amplify the entire sequence of the sex specific semisynthetic amplicon. The sequence of the synthetic oligonucleotide primers is as given below in SEQ ID NO:2, SEQ ID NO:3, SEQ ID NO:4 and SEQ ID NO:5.

SEQ ID NO:2   5'GGATCCCTATTAGTGTAAGGG3'

SEQ ID NO:3   5'GGATCCCTTTTGCACTCTGCTG3'

SEQ ID NO:4   5'GGATCCCTATTAGTG3'

SEQ ID NO:5   5'GGATCCCTTTTGCACTC3'

The isolated DNA samples of the cultivar PUSA-GIANT were quantified spectrophotometrically and subjected to sequence tagged site polymerase chain reaction by using two, pairs of synthetic oligonucleotide primers so as to simultaneously amplify sex specific and gender-neutral semisynthetic amplicons. The sequence of the synthetic oligonucleotide primers used in the present invention for the preparation of gender-neutral amplicon are

SEQ ID NO:6 5'CGAAATCGGTAGACGATACG 3' and

SEQ ID NO:7 5' GGGGATAGAGGGACTTGAAC 3'

[SEQ ID NOs:6 and 7 are as described by Taberlet et al. (*PMB* 17:1105–1109, 1991)].

The reaction mixture contained, 50ng of template DNA, 1.5 mM MgCl2, 50 mM KCI, 10 mM TAPS [3-tri (hydroxymethyl) methyl amino propane sulphonic acid], 0.01 % gelatine, 200 µM of each dATP, dCTP, dGTP and dTTP, 50 µM spermidine, 1.0 units of thermostable DNA polymerase, 75ng of each of synthetic oligonucleotide primers having sequence 5'GGATCCCTATTAGTGTAAGGG 3' (SEQ ID NO:2) and 5'GGATCCCTTTTGCACTCTGCTG 3' (SEQ ID NO:3), 12.5ng of each of synthetic oligonucleotide primer having the sequence 5'CGAAATCGGTAGACGATACG 3' (SEQ ID NO:6) and 5'GGGGATAGAGGGACTTGAAC 3' (SEQ ID NO:7). The final volume was made up to 25 µl by adding sterile water. The reaction mixture was then overlaid with 30 µl of mineral oil and spun for 30 sec. at 1000rpm. Amplification reaction was performed in a thermocycler, where the reaction mixture was incubated at 94° C. for 4 minutes, followed by 30 cycles of 94° C. for 45 seconds, 55° C. for 1 minute and 72° C. for 2 minutes each. The amplification reaction was concluded by a final extension of 72° C. for 5 minutes. The amplification product was analyzed on a 1.5% neutral agarose horizontal slab gel in TAE buffer, (0.09M Tris-acetate and 2 mM EDTA) at a constant current. After electrophoresis, gel was stained with ethidium bromide (1 µg/ml) and was visualized on a long wavelength (302 nm) UV transilluminator.

It was observed, that on using the said pairs of synthetic oligonucleotide primers in a sequence tagged site polymerase chain reaction, all the male DNA samples revealed presence of two semisynthetic amplicons, one sex specific amplicon of 831 bp (base pairs) in size while the other being gender-neutral amplicon 0.6kb in size. The female DNA samples showed a single gender-neutral semisynthetic amplicon, 0.6kb in size. Thus, the simultaneous preparation of sex specific and gender-neutral semisynthetic amplicons could identify male and female papaya plants to the extent of 95% accuracy.

The following examples 2 and 3 relate to the determination of sex in dioecious cultivars of papaya by simultaneously preparing sex specific and gender-neutral semisynthetic amplicons.

EXAMPLE NO. 2

Matured male and female plants of dioecious papaya cultivars namely, CO-2, CO-4, CO-5, CO-6, MF-1, PANT-1, WASHINGTON, PUSA-GIANT and PUSA-DWARF were identified in the field. Young leaf tissue from both male and female individuals of these cultivars was harvested frozen in liquid nitrogen. Ten grams of this frozen tissue of each sample was mechanically ground to a fine powder using a pestle and mortar in liquid nitrogen.

The DNA isolations were carried out by Roger and Bendich method (Roger, 1988, PMB manual, A6:1 Ed), where 15 ml of extraction buffer containing 2% CTAB (Cetyltriethyl ammonium bromide), 100 mM Tris-HCI (pH 8.0), 20 mM EDTA (pH 8.0), 1.4 M NaCI, and 1% polyvinyl pyrrolidone was added per 10gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1M NaCI, 10 mM Tris-HCI (pH 8.0), 1 mM EDTA (pH 8.0)] and was precipitated with twice the volume of absolute ethanol. The DNA precipitate was washed with 70% ethanol, centrifuged and the pellet was redissolved in TE buffer [10 mM Tris-HCI (pH 8.0), 1 mM EDTA (pH 8.0)]. For removal of RNA, the DNA was incubated at 37° C. for 1 hour with the enzyme RNaseA.

The isolated DNA samples were quantified spectrophotometrically and were subjected to sequence tagged site polymerase chain reaction by using two pairs of synthetic oligonucleotide primers so as to simultaneously amplify sex specific and gender-neutral semisynthetic amplicons.

The reaction mixture contained, 50ng of template DNA, 1.5 mM MgCl2, 50 mM KCI, 10 mM TAPS [3-tri (hydroxymethyl) methyl amino propane sulphonic acid], 0.01% gelatine, 200 FM of each dATP, dCTP, dGTP and dITP, 50pM spermidine, 1.0 units of thermostable DNA polymerase, 75ng of each of synthetic oligonucleotide primers having sequence—5'GGATCCCTATTAGTGTAAGGG 3' (SEQ ID NO:2) and 5'GGATCCCTTTTGCACTCTGCTG 3' (SEQ ID NO:3), 12.5ng of each of synthetic oligonucleotide primer having the sequence 5'CGAAATCGGTAGACGATACG 3' (SEQ ID NO:6) and 5'GGGGATAGAGGGACTTGAAC 3' (SEQ ID NO:7). The final volume was made up to 25 µl by adding sterile water. The reaction mixture was then overlaid with 30 µl of mineral oil and spun for 30 sec. at 1000rpm.

Amplification reaction was performed in a thermocycler, where the reaction mixture was incubated at 94° C. for 4 minutes, followed by 30 cycles of 94° C. for 45 seconds, 55° C. for 1 minute and 72° C. for 2 minutes each. The amplification reaction was concluded by a final extension of 72° C. for 5 minutes. The amplification product was analyzed on a 1.5% neutral agarose horizontal slab gel in TAE buffer, (0.09M Tris-acetate and 2 mM EDTA) at a constant current. After electrophoresis, gel was stained with ethidium bromide (1 µg/ml) and was visualised on a long wavelength (302 nm) UV transilluminator.

It was observed, that on using the said pairs of synthetic oligonucleotides in a sequence tagged site polymerase chain reaction, all the male DNA samples revealed presence of two semisynthetic amplicons, one sex specific amplicon of 831 bp (base pairs) in size while the other being gender-neutral amplicon 0.6kb in size. The female DNA samples showed a single gender-neutral semisynthetic amplicon, 0.6kb in size. Thus, the simultaneous preparation of sex specific and gender-neutral semisynthetic amplicons could accurately identify male and female papaya plants in all the dioecious cultivars tested.

EXAMPLE NO. 3

Male and female plants of dioecious papaya cultivars namely, CO-2, CO-4, CO-5, CO-6, MF-1, PANT-1, WASHINGTON, PUSA-GIANT and PUSA-DWARF were identified in the field. Leaf tissue from male and female individuals of these cultivars was harvested in the form of leaf discs and then frozen in liquid nitrogen, in sterile, 1.5 ml microcentrifuge tubes.

The leaf discs, weighing 10 mg were used for DNA isolation, which was carried out by modifying the method described by Thompson et al, Biotechniques, Vol. 19, No. 3, 1995, 394–400. Fifty microliters of extraction buffer containing 100 mM Tris-HCI (pH 9.5), 1M KCI and 5 mM EDTA was added per 10 mg of plant tissue in 1.5 ml microcentrifuge tubes. The tubes were further incubated at 95° C. for 20 min in a dry bath. The contents were mixed intermittently by inverting and tapping the tubes. After incubation, the tubes were placed on ice for 5 min. the DNA thus isolated was diluted by adding 120 µl of dilution buffer containing 10mM Tris (pH9.0), 1 mM EDTA (pH 8.0) and 0.1 mg RNaseA.

The diluted supernatant was directly used in the polymerase chain reaction. The final volume of reaction mixture was 25 µl, which contained 5 µl of the diluted supernatant, 1.5 mM MgCl2, 50 mM KCI, 10 mM TAPS [3-tri (hydroxymethyl) methyl amino propane sulphonic acid], 0.01% gelatine, 200 µm of each dATP, dCTP, dGTP and dITP, 50pM spermidine, 1.0 Units of thermostable DNA polymerase, and 75ng of each of synthetic oligonucleotide primers having sequence 5'GGATCCCTATTAGTG 3' (SEQ ID NO:4) and 5'GGATCCClllTGCACTC 3' (SEQ ID NO:5), 12.5ng of each of synthetic oligonucleotide primer having the sequence 5'CGAAATCGGTAGACGATACG 3' (SEQ ID NO:6) and 5'GGGGATAGAGGGACTTGAAC 3' (SEQ ID NO:7). The final volume was made up to 25 µl by adding sterile water. The reaction mixture was then overlaid with 30 µl of mineral oil and spun for 30 sec. at 10000rpm. Amplification reaction was performed in a thermocycler. The reaction mixture was initially incubated at 94° C. for 4 minutes, followed by 30 cycles of 94° C. for 45 seconds, 45 C. for 1 minute and 72° C. for 2 minutes each. The amplification reaction was concluded by a final extension of 72° C. for 5 minutes. The amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide (1 µg/ml) and was visualised on a long wavelength (302 nm) UV transilluminator.

It was observed, that on using the said pairs of synthetic oligonucleotides in a sequence tagged site polymerase chain reaction, all the male DNA samples revealed presence of two semisynthetic amplicons, one sex specific amplicon of 831 bp (base pairs) in size while the other being gender-neutral amplicon 0.6kb in size. The female DNA samples showed a single gender-neutral semisynthetic amplicon, 0.6kb in size. Thus, the simultaneous preparation of sex specific and gender-neutral semisynthetic amplicons could accurately identify male and female papaya plants in all the dioecious cultivars tested.

Following examples 4 and 5 relate to the sex determination in wild species of the genus Carica, by simultaneous preparation of sex specific and gender-neutral semisynthetic amplicons.

EXAMPLE NO. 4

Male and female plants of wild species, *Carica cauliflora* were identified in the field. Young leaf tissue from both male and female individuals was harvested and frozen in liquid nitrogen. Ten grams of this frozen tissue of each sample was mechanically ground to a fine powder using a pestle and mortar in liquid nitrogen.

The DNA isolations were carried out by Roger and Bendich method (Roger, 1988, PMB manual, A6:1 Ed), where 15 ml of extraction buffer containing 2% CTAB (Cetyltriethyl ammonium bromide), 100 mM Tri-HCI (pH 8.0), 20 mM EDTA (pH 8.0), 1.4 M Nacl, and 1% polyvinyl pyrrolidone was added per 10gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1 M NaCI, 10 mM Tris-HCI (pH 8.0)1mM EDTA (pH 8.0)] and was precipitated with twice the volume of absolute ethanol. The DNA precipitate was washed with 70% ethanol, centrifuged and the pellet was redissolved in TE buffer [10 mM Tris-HCI (pH 8.0), 1 mM EDTA (pH 8.0)]. For removal of RNA, the DNA was incubated at 37° C. for 1 hour with the enzyme RNaseA.

The isolated DNA samples were quantified spectrophotometrically and were subjected to sequence tagged site polymerase chain reaction.

The reaction mixture contained; 50ng of template DNA, 1.5 mM MgCl2, 50 mM KCI, 10 mM TAPS [3-tri (hydroxymethyl) methyl amino propane sulphonic acid], 0.01% gelatine, 200 PM of each dATP, dCTP, dGTP and dITP, 50pM spermidine, 1.0 units of thermostable DNA polymerase, 75ng of each of synthetic oligonucleotide primers having sequence 5'GGATCCCTATTAGTGTAAGGG 3' (SEQ ID NO:2) and 5'GGATCCCTTTTGCACTCTGCTG 3' (SEQ ID NO:3), 12.5ng of each of synthetic oligonucleotide primer having the sequence 5'CGAAATCGGTAGAC-GATACG 3' (SEQ ID NO:6) and 5'GGGGATAGAGG-GACTTGAAC 3' (SEQ ID NO:7). The final volume was made up to 25 µl by adding sterile water. The reaction mixture was then overlaid with 30 µl of mineral oil and spun for 30 sec. at 1000rpm.

Amplification reaction was performed in a thermocycler, where the reaction mixture was incubated at 94° C. for 4 minutes, followed by 30 cycles of 94° C. for 45 seconds, 55° C. for 1 minute and 72° C. for 2 minutes each. The amplification reaction was concluded by a final extension of 72° C. for 5 minutes. The amplification product was analyzed on a 1.5% neutral agarose horizontal slab gel in TAE buffer, (0.09M Tris-acetate and mM EDTA) at a constant current. After electrophoresis, gel was stained with ethidium bromide (1 µg/ml) and was visualised on a long wavelength (302 nm) UV transilluminator.

It was observed, that on using the said pairs of synthetic oligonucleotides in a sequence tagged site polymerase chain reaction, all the male DNA samples revealed presence of two semisynthetic amplicons, one sex specific amplicon of 831 bp (base pairs) in size while the other being gender-neutral amplicon 0.6kb in size. The female DNA samples showed a single gender-neutral semisynthetic amplicon, 0.6kb in size. Thus, the simultaneous preparation of sex specific and gender-neutral semisynthetic amplicons could accurately identify male and female papaya plants of the dioecious wild species tested.

EXAMPLE NO. 5

Male and female plants of wild species, *Carica cauliflora* were identified in the field. Leaf tissue from male and female individuals was harvested in the form of leaf discs and then frozen in liquid nitrogen, in sterile, 1.5 ml microcentrifuge tubes.

The leaf discs, weighing 10 mg were used for DNA isolation, which was carried out by modifying the method described by Thompson et al, Biotechniques, Vol. 19, No. 3, 1995, 394–400. Fifty microliters of extraction buffer containing 100 mM Tris-HCI (pH 9.5), 1M KCI and 5 mM EDTA was added per 10 mg of plant tissue in 1.5 ml microcentrifuge tubes. The tubes were further incubated at 95° C. for 20 min. in a dry bath. The contents were mixed intermittently by inverting and tapping the tubes. After incubation, the tubes were placed on ice for 5 min. the DNA thus isolated was diluted by adding 120 pl of dilution buffer containing 10mM Tris (pH9.0), 1 mM EDTA (pH 8.0) and 0.1 mg RNaseA.

The diluted supernatant was directly used in the polymerase chain reaction. The final volume of reaction mixture was 25 μl, which contained 5 μl of the diluted supernatant, 1.5 mM MgCl2, 50 mM KCl, 10 mM TAPS [Stri (hydroxymethyl)methyl amino propane sulphonic acid], 0.01% gelatine, 200 FM of each dATP, dCTP, dGTP and dITP, 50 μM spermidine, 1.0 Units of thermostable DNA polymerase, and 75ng of each of synthetic oligonucleotide primers having sequence 5'GGATCCCTATTAGTG 3' (SEQ ID NO:4) and 5'GGATCCCTTTTGCACTC 3' (SEQ ID NO:5), 12.5ng of each of synthetic oligonucleotide primer having the sequence 5'CGAAATCGGTAGACGATACG 3' (SEQ ID NO:6) and 5'GGGGATAGAGGGACTTGAAC 3' (SEQ ID NO:7). The final volume was made up to 25 μl by adding sterile water. The reaction mixture was then overlaid with 30 μl of mineral oil and spun for 30 sec. at 1000 rpm.

Amplification reaction was performed in a thermocycler. The reaction mixture was initially incubated at 94° C. for 4 minutes, followed by 30 cycles of 94° C. for 45 seconds, 45° C. for 1 minute and 72° C. for 2 minutes each. The amplification reaction was concluded by a final extension of 72° C. for 5 minutes. The amplification products were then analyzed on 1.5% neutral agarose horizontal slab gels in TAE buffer, (0.09M Trisacetate and 2 mM EDTA) at a constant current of 40 mA. After electrophoresis, the gel was stained in dark with ethidium bromide (1 μg/ml) and was visualised on a long wavelength (302 nm) UV transilluminator.

It was observed, that on using the said pairs of synthetic oligonucleotides in a sequence tagged site polymerase chain reaction, all the male DNA samples revealed presence of two semisynthetic amplicons, one sex specific amplicon of 831 bp (base pairs) in size while the other being gender-neutral amplicon 0.6kb in size. The female DNA samples showed a single gender-neutral semisynthetic amplicon, 0.6kb in size. Thus, the simultaneous preparation of sex specific and gender-neutral semisynthetic amplicons could accurately identify male and female papaya plants of the dioecious wild species tested.

The following examples 6 and 7 relate to the sex determination of papaya plants of unknown sex at the seedling stage, by simultaneous preparation of sex specific and gender-neutral semisynthetic amplicons.

EXAMPLE NO. 6

Fifty seedling plants were serially numbered 1–50 in the field. Young leaf tissue of 25 randomly selected individuals was harvested frozen in liquid nitrogen. One gram of this frozen tissue of each sample was mechanically ground a fine powder using a pestle and mortar in liquid nitrogen.

The DNA isolations were carried out by Roger and Bendich method (Roger, 1988, PMB manual, A6:1 Ed), where 15 ml of extraction buffer containing 2% CTAB (cetyltriethyl ammonium bromide), 100 mM Tri-HCI (pH 8.0), 20 mM EDTA (pH 8.0), 1.4 d. INacl, and 1% polyvinyl pyrrolidone was added per 10gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [I M NaCI, 10 mM Tris-HCI (pH 8.0)1 mM EDTA (pH 8.0)] and was precipitated with twice the volume of absolute ethanol. The DNA precipitate was washed with 70% ethanol, centrifuged and the pellet was redissolved in TE buffer [10 mM Tris-HCI (pH 8.0), 1 mM EDTA (pH 8.0)]. For removal of RNA, the DNA was incubated at 37° C. for 1 hour with the enzyme RNaseA.

The isolated DNA samples were quantified spectrophotometrically and were subjected to sequence tagged site polymerase chain reaction.

The reaction mixture contained, 50ng of template DNA, 1.5 mM MgCl2, 50 mM KCl, 10 mM TAPS [3-tri (hydroxymethyl)methyl amino propane sulphonic acid], 0.01% gelatine, 200μM of each dATP, dCTP, dGTP and dTTP, 50 μM spermidine, 1.0 units of thermostable DNA polymerase, 75ng of each of synthetic oligonucleotide primers having sequence 5'GGATCCCTATTAGTGTAAGGG 3' (SEQ ID NO:2) and 5'GGATCCCTTTTGCACTCTGCTG 3' (SEQ ID NO:3), 12.5ng of each of synthetic oligonucleotide primer having the sequence 5'CGAAATCGGTAGAC-GATACG 3' (SEQ ID NO:6) and 5'GGGGATAGAGG-GACTTGAAC 3' (SEQ ID NO:7). The final volume was made up to 25 μl by adding sterile water. The reaction mixture was then overlaid with 30 μl of mineral oil and spun for 30 sec. at 1000 rpm.

Amplification reaction was performed in a thermocycler, where the reaction mixture was incubate at 94° C. for 4 minutes, followed by 30 cycles of 94° C. for 45 seconds, 55° C. for 1 minute and 72° C. for 2 minutes each. The amplification reaction was concluded by a final extension of 72° C. for 5 minutes. The amplification product was analyzed on a 1.5% neutral agarose horizontal slab gel in TAE buffer, (0.09M Tris-acetate and 2 mM EDTA) at a constant current. After electrophoresis, gel was stained with ethidium bromide (1 μg/ml) and was visualised on a long wavelength (302 nm) UV transilluminator.

The results obtained were compared with the sex of the plant observed after flowering. The results are tabulated in the following table.

| Serial No. of Seedling Plant | Sex of the Plant Determined by the Process | Sex of the Plant Observed (in the field) After Flowering |
| --- | --- | --- |
| 4 | Male | Male |
| 5 | Female | Female |
| 8 | Female | Female |
| 10 | Male | Male |
| 12 | Male | Male |
| 13 | Female | Female |
| 16 | Female | Female |
| 18 | Male | Male |
| 22 | Male | Male |
| 26 | Male | Male |
| 27 | Male | Male |
| 29 | Female | Female |
| 30 | Male | Male |
| 32 | Female | Female |
| 33 | Female | Female |
| 34 | Male | Male |
| 36 | Female | Female |
| 37 | Male | Male |
| 38 | Male | Male |
| 41 | Female | Female |
| 43 | Male | Male |
| 47 | Female | Female |
| 49 | Female | Female |
| 50 | Female | Female |

It was observed, that on using the said pairs of synthetic oligonucleotides in a sequence tagged site polymerase chain reaction, all the DNA samples which revealed presence of two semisynthetic amplicons: one sex specific, 831 bp (base pairs) in size while the other being gender-neutral 0.6kb in size were males, whereas the DNA samples which showed a single gender-neutral semisynthetic amplicon, 0.6kb in size were females.

Thus, the simultaneous preparation of sex specific and gender-neutral semisynthetic amplicons could accurately identify male and female papaya plants at the seedling stage.

EXAMPLE NO: 7

Fifty seedling plants were serially numbered 1–50 in the field. Young leaf tissue of 22 randomly selected individuals was harvested frozen in liquid nitrogen. Leaf tissue from these individuals was harvested in the form of leaf discs and then frozen in liquid nitrogen in sterile, 1.5 ml microcentrifuge tubes. The leaf discs, weighing 10 mg were used for DNA isolation, which was carried out by modifying the method described by Thompson et al, *Biotechniques,* Vol. 19, No. 3, 1995, 394400. Fifty microliters of extraction buffer containing 100 mM Tris-HCl (pH 9.5), 1 M KCl and 5 mM EDTA was added per 10 mg of plant tissue in 1.5 ml microcentrifuge tubes. The tubes were further incubated at 95° C. for 20 min. in a dry bath. The contents were mixed intermittently by inverting and tapping the tubes. After incubation, the tubes were placed on ice for 5 min. The DNA thus isolated was diluted by adding 120 μl of dilution buffer containing 10 mM Tris (pH9.0), 1 mM EDTA (pH 8.0) and 0.1 mg RNaseA.

The diluted supernatant was directly used in the polymerase chain reaction. The final volume of reaction mixture was 25 μl, which contained 5 μl of the diluted supernatant, 1.5 mM MgCl2, 50 mM KCl, 10 mM TAPS [3-tri(hydroxymethyl)methyl amino propane sulphonic acid], 0.01% gelatine, 200 μM of each dATP, dCTP, dGTP and dlTP, 50 μM spermidine, 1.0 Units of thermostable DNA polymerase, and 75ng of each of synthetic oligonucleotide primers having sequence 5'GGATCCCTATTAGTG 3' (SEQ ID NO:4) and 5'GGATCCCTTTTGCACTC 3' (SEQ ID NO:5), 12.5ng of each of synthetic oligonucleotide primer having the sequence 5'CGAAATCGGTAGACGATACG 3' (SEQ ID NO:6) and 5'GGGGATAGAGGGACTTGAAC 3' (SEQ ID NO:7). The final volume was made up to 25 μl by adding sterile water. The reaction mixture was then overlaid with 30 μl of mineral oil and spun for 30 sec. at 1000 rpm.

Amplification reaction was performed in a thermocycler. The reaction mixture was initially incubated at 94° C. for 4 minutes, followed by 30 cycles of 94° C. for 45 seconds, 45° C. for 1 minute and 72° C. for 2 minutes each. The amplification reaction was concluded by a final extention of 72° C. for 5 minutes. The amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide (1pg/ml) and was visualised on a long wavelength (302 nm) UV transilluminator.

The results obtained were compared with the sex of the plant observed after flowering. The results are tabulated in the following table.

| Serial No. of Seedling Plant | Sex of the Plant Determined by the Process | Sex of the Plant Observed (in the field) After Flowering |
| --- | --- | --- |
| 1 | Male | Male |
| 6 | Male | Male |
| 7 | Female | Female |
| 9 | Male | Male |
| 11 | Male | Female |
| 14 | Male | Male |
| 15 | Female | Female |
| 17 | Female | Female |
| 19 | Female | Female |
| 20 | Female | Female |
| 21 | Female | Female |
| 23 | Female | Female |
| 24 | Male | Male |
| 26 | Male | Male |
| 28 | Female | Female |
| 35 | Male | Male |
| 39 | Male | Male |
| 40 | Male | Male |
| 42 | Male | Male |
| 44 | Male | Male |
| 45 | Male | Male |
| 46 | Female | Female |

It was observed, that on using the said pairs of synthetic oligonucleotides in a sequence tagged site polymerase chain reaction, ail the DNA samples which revealed presence of two semisynthetic amplicons: one sex specific, 831 bp (base pairs) in size while the other being gender-neutral 0.6kb in size were males, whereas the DNA samples which showed a single gender-neutral semisynthetic amplicon, 0.6kb in size were females.

Thus the simultaneous preparation of sex specific and gender-neutral semisynthetic amplicons could accurately identify male and female papaya plants at the seedling stage.

ADVANTAGES OF THE PRESENT INVENTION

1. The important advantage is to provide process for simultaneous preparation of sex specific and gender-neutral semisynthetic amplicons; useful for sex determination of dioecious papaya plant.

2. The present invention will be highly useful in intra and interspecific breeding experiments, and for screening the F1 and F2 generations for male and female plants.

3. With this invention, the sex of the papaya plants can be identified before flowering, allowing direct transplantation and distribution of only the identified female plants.

4. The said process is fast, accurate, does not involve any hazardous chemicals.

5. The genotype of the plant is not affected in the process of identification of sex of the plant.

6. The said process requires minimal amount of sample material.

7. The process is very much cost effective and a large number of samples can be processed in a very short duration.

8. Environmental and seasonal variations do not interfere in the process for simultaneous preparation of sex specific and gender-neutral semisynthetic amplicons.

What is claimed is:

1. A method for sex determination of a dioecious papaya plant by the simultaneous preparation of a male sex-specific semisynthetic amplicon and a gender-neutral semisynthetic amplicon comprising amplifying nucleic acids islolated from any part of a papaya plant in a polymerase chain reaction using (i) a pair of male sex-specific synthetic oligonucleotides that specificially anneal to and specifically amplify the male sex-specific sequence of SEQ ID NO:1 to produce a male sex-specific semisynthetic amplicon, and (ii) a pair of gender-neutral synthetic oligonucleotides that specificially anneal to and specifically amplify a gender-neutral sequence to produce a gender-neutral semisynthetic amplicon, wherein following amplification the presence of the male sex-specific semisynthetic amplicon and the gender-neutral semisynthetic amplicon indicates that the papaya plant is male, and the presence of only the gender-neutral amplicon indicates that the papaya plant is female.

2. The method of claim 1, wherein the pair of male sex-specific synthetic oligonucleotides is SEQ ID NO:2 and 3, or SEQ ID NO: 4 and 5.

3. The method of claim 2, wherein the male sex-specific semisynthetic amplicon is 831 bp in size.

4. The method claim 1, wherein the gender-neutral synthetic oligonucleotides are SEQ ID NOs:6 and 7.

5. The method of claim 1, wherein the gender-neutral semisynthetic amplicon is 600 bp in size.

6. The method of claim 1, wherein the male sex-specific semisynethic amplicon and the gender-neutral semisynthetic amplicon differ in size to allow for differentiation between the amplicons.

7. The method of claim 6, wherein the amplicons are differentiated by resolving on agarose gel, polyacrylamide gel, or a mixture of polyacrylamide and agarose.

8. The method of claim 1, wherein the nucleic acids are from a papaya plant at a juvenile stage.

9. The method of claim 1, wherein any or all of the oligonucleotides are labeled.

10. The method of claim 9, wherein the label with which any or all of the oligonucleotides are labeled is radioactive or non-radioactive.

11. The method of claim 10, wherein the label is a radioactive label and wherein the radioactive label is $^{32}P$, $^{3}H$, $^{14}C$, or $^{125}I$.

12. The method of claim 10, wherein the label is a non-radioactive label and wherein the non-radioactive label is an alkaline phosphate, a biotin bromodeoxyuridine, a fluorescent molecule, or a chromogenic molecule.

* * * * *